United States Patent [19]

Yano et al.

[11] Patent Number: 5,129,443
[45] Date of Patent: * Jul. 14, 1992

[54] METHOD OF MANUFACTURING A PRODUCT BY ESTIMATING THERMAL STRESS USING A MODEL OF THE PRODUCT MADE OF DIFFERENT MATERIAL

[75] Inventors: Mitsuru Yano, Okagaki; Hisashi Yasuda; Masatoshi Nakamizo, both of Kitakyusyu; Takashi Hattori, Kanda; Kenji Itoh, Moka, all of Japan

[73] Assignee: Hitachi Metals, Ltd., Tokyo, Japan

[*] Notice: The portion of the term of this patent subsequent to Sep. 17, 2008 has been disclaimed.

[21] Appl. No.: 725,452

[22] Filed: Jul. 3, 1991

Related U.S. Application Data

[63] Continuation of Ser. No. 500,952, Mar. 29, 1990, Pat. No. 5,048,346.

[51] Int. Cl.$^5$ .................. B22D 15/00; B22D 46/00; G01B 5/30; G01N 25/72; G01N 3/60
[52] U.S. Cl. .................... 164/4.1; 73/804; 73/866.4; 374/5; 374/57; 374/142
[58] Field of Search .............. 73/866.4, 804; 374/57, 374/4, 5, 45, 142; 164/4.1

[56] References Cited

U.S. PATENT DOCUMENTS

| | | | |
|---|---|---|---|
| 3,274,652 | 9/1966 | Banks | 164/4.1 |
| 3,964,313 | 6/1976 | Connick | 374/134 |
| 4,304,286 | 12/1981 | Waldron | 164/4.1 |
| 4,711,131 | 12/1987 | Hopkins | 73/866.4 |

FOREIGN PATENT DOCUMENTS

| | | | |
|---|---|---|---|
| 0336829 | 10/1989 | European Pat. Off. | 73/804 |
| 0048253 | 10/1985 | Japan | 164/4.1 |
| 2259038 | 11/1987 | Japan | 73/866.4 |
| 0208898 | 1/1968 | U.S.S.R. | 164/4.1 |
| 0337696 | 5/1972 | U.S.S.R. | 164/4.1 |
| 0585427 | 12/1977 | U.S.S.R. | 73/804 |
| 1357781 | 12/1987 | U.S.S.R. | 73/866.4 |

OTHER PUBLICATIONS

Ivanov et al., "Thermomechanical Fatigue Under Combined and Independent Thermal and Mechanical Loads", Ind. Labs. (USA), vol. 45, No. 9 (Mar. 1980).
Stanley, P. et al., "Appraisal of a Photothermoelastic Technique for Transient Two-Dimensional Thermal Stresses", J. Phys. E. Instrum., vol. 13 (1980).

Primary Examiner—William A. Cuchlinski, Jr.
Assistant Examiner—Diego F. F. Gutierrez
Attorney, Agent, or Firm—Finnegan, Henderson, Farabow, Garrett & Dunner

[57] ABSTRACT

A method of manufacturing a heat resistant member includes the step of designing the shape of the heat resistant member, including the substeps of estimating thermal stress of the heat resistant member by heating a model formed by a high-thermal expansion material which has a similar shape to the desired shape of the heat resistant member while the model is restrained and also while it is free. The high-thermal expansion material is different from the material of the member being modeled and has a thermal expansion coefficient greater than that of the material of the member being modeled. Additionally, the step of designing includes the substeps of measuring the strain of the model at each of a plurality of predetermined positions while the model is heated by strain gauges adhered to predetermined positions on the model, and calculating the stress at each predetermined position from the difference in measured strain values between the restraint state and the free state. Finally, the manufacturing method includes casting the heat resistant member to the designed shape.

15 Claims, 1 Drawing Sheet

METHOD OF MANUFACTURING A PRODUCT BY ESTIMATING THERMAL STRESS USING A MODEL OF THE PRODUCT MADE OF DIFFERENT MATERIAL

This is a continuation of application Ser. No. 07/500,952, filed Mar. 29, 1990, now U.S. Pat. No. 5,048,346.

BACKGROUND OF THE INVENTION

The present invention relates to a method of estimating the thermal stress of a heat-resistant member, part or the whole of which is to be heated to such a high temperature as 500° C. or higher.

Heat-insulating members repeatedly placed under heated and cooled conditions, for instance, exhaust gas equipment such as exhaust manifolds used in internal combustion engines of automobiles, etc., are required to be designed such that they undergo a minimum thermal strain, to prevent their breakage such as by cracking during operation. For instance, in the case of exhaust manifolds of automobiles, they are subjected to increasingly higher temperatures and thermal loads, because engines having increasingly higher performance have been developed. Therefore, the exhaust manifolds should be designed such that thermal cracks are prevented from being generating due to thermal strains.

Conventionally, the measurement of a thermal strain distribution of a manifold, etc. is conducted by using high-temperature strain gauges as disclosed in Japanese Patent Publication No. 51-42947 when the temperature of measurement is 200° C. or higher. However, the high-temperature strain gauges have high stiffnesses and suffer from thermal strain because they are attached to the measurement sites of a manifold by welding. Accordingly, in portions having small radii of curvature, reliable data cannot be obtained due to the gauges peeling off from the measurement sites. Further, even with the above strain gauges, the linearity of measurement data will be lost at a temperature higher than 500° C. Therefore, the strain distribution on the overall manifold surface at a high temperature was conventionally presumed from data at 500° C. or lower.

In addition, in the above method, test samples are produced by casting and subjected to a bench test, and the modification of cast product designs is conducted based on the data obtained with respect to cast samples. Accordingly, such a method requires a long period of time for determining the best design of a heat-resistant member such as an exhaust manifold, resulting in high development costs.

OBJECT AND SUMMARY OF THE INVENTION

Accordingly, an object of the present invention is to provide the method of estimating a thermal stress of a heat-resistant member which is to be heated to a temperature of 500° C. or higher with high reliability and efficiency, without resorting to test samples made of the same metal materials as the heat-resistant member.

As a result of intense research in view of the above object, the inventors have found that the thermal stress distribution of the heat-resistant member can be estimated with high reliability by using a model formed by a high-thermal expansion material and having a shape similar to that of the heat-resistant member to be measured, and heating this model for thermal stress measurement. The present invention is based on this finding.

Thus, the method of estimating a thermal stress of a heat-resistant member according to the present invention comprises heating a model formed by a high-thermal expansion material and having a shape similar to that of the heat-resistant member; and measuring a thermal strain of the model at each of a plurality of predetermined positions by strain gauges adhered thereto.

Particularly, by measuring stress while heating the model both in a restraint state and in a free state, or by measuring stress while cooling the model from a high temperature to a low temperature both in a restraint state and in a free state, it is possible to obtain an extremely reliable thermal stress distribution.

Further, more exact results are obtained where stress is measured both in a restraint state and in a free state, in a heated state and in a cooled state, respectively.

Further, much more exact results are obtained by measuring the temperature of the model by a temperature sensor, correcting the strain values measured by the strain gauges by the temperature measured by the temperature sensor, and calculating a true stress at each measurement temperature.

DETAILED DESCRIPTION OF THE INVENTION

Figure 1:
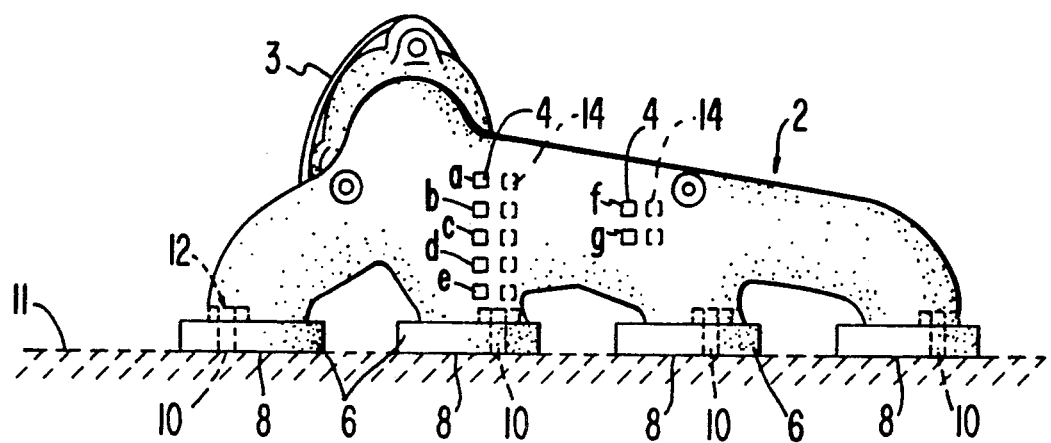
FIG. 1 is a front view showing a model used in the method of the present invention.

In the present invention, a model having a shape similar to that of a heat-resistant member to be measured is formed by a material having a thermal expansion coefficient several tens times as large as that of the heat-resistant member. Such model material is preferably a hard foam material such as a polyurethane foam having a thermal expansion coefficient 20-25 times as large as that of spheroidal graphite cast iron. When a polyurethane foam model is used, the same thermal expansion as that of spheroidal graphite cast iron is obtained when heated to a temperature on the level of 1/20-1/25 that of the spheroidal graphite cast iron. Specifically, if a manifold made of spheroidal graphite cast iron is heated to 800° C. during operation, the same thermal expansion as that of the spheroidal graphite cast iron can be obtained in a polyurethane foam model when heated only to 32°-40° C. This temperature range is derived from the equation: 800×1/(20-25)=32-40. In addition, the polyurethane foam is easily worked to a desired shape.

The polyurethane foam is produced by a continuous foaming process, and has high uniformness in density (0.03-0.10 g/cm$^3$). Further, it is expanded relatively slowly when heated.

In one embodiment of the present invention, the thermal stress of a heat-resistant member is estimated by heating a model formed by a high-thermal expansion material and having a shape similar to that of the heat-resistant member; and measuring a thermal strain of the model at each of a plurality of predetermined positions by strain gauges adhered thereto.

In another embodiment of the present invention, the thermal stress of a heat-resistant member is estimated by heating a model formed by a high-thermal expansion material and having a shape similar to that of the heat-resistant member in a restraint state and a free state, respectively; measuring the strain of the model at each of a plurality of predetermined positions in the heated state in both the restrained and free states, by strain gauges gauges adhered to the predetermined positions of the model; and calculating a stress at each predetermined position from the difference in the strain value between the restraint state and the free state, thereby estimating the stress of the heat-resistant member in a heated state.

In a further embodiment of the present invention, the thermal stress of a heat-resistant member is estimated by cooling a model formed by a high-thermal expansion material and having a shape similar to that of the heat-resistant member in a restraint state and a free state, respectively, from a high temperature to a low temperature; measuring the strain of the model at each of a plurality of predetermined positions in a cooled state, by strain gauges adhered to the predetermined positions of the model; and calculating a stress at each predetermined position from the difference in a strain value between the restraint state and the free state, thereby estimating the stress of the heat-resistant member in a cooled state.

In a still further embodiment of the present invention, the thermal stress of a heat-resistant member is estimated by heating a model formed by a high-thermal expansion material and having a shape similar to that of the heat-resistant member in a restraint state and a free state, respectively, from a low temperature to a high temperature; measuring the strain of the model at each of a plurality of predetermined positions in a heated state; cooling the model with or without restraint; measuring the strain of the model at each of predetermined positions in a cooled state; and calculating stresses at each predetermined position both in a heated state and in a cooled state, from the differences in a strain value between the restraint state and the free state, thereby estimating the stresses of the heat-resistant member both in a heated state and in a cooled state.

In a still further embodiment of the present invention, the strain value of the model measured by the strain gauge is corrected by a temperature measured at each predetermined position, thereby calculating the true stress value of the model at a predetermined temperature.

The measurement method according to each embodiment of the present invention will be described in detail referring to FIG. 1.

A manifold model 2 made of a polyurethane foam is placed on table 11 (shown schematically) and adhered with a plurality of strain gauges 4, 4, .... An exhaust gas outlet 3 of the manifold model 2 is connected to an exhaust gas pipe (not shown). It is placed in a restraint state by fixing its flange portions onto the table by bolts 12 (also shown schematically), and then heated by blowing hot air into the model 2 through ports 8, 8, .. . by a drier (not shown) such that the surface temperature of the model 2 reaches about 50° C. At this high temperature and in a restraint state, strain values $\epsilon_1$ are measured at various predetermined measurement sites a, b, c, .... Next, in a free state where the flange portions 6, 6, . . . are not fixed, the polyurethane model 2 is similarly heated to measure strain values $\epsilon_2$ at various measurement sites a, b, c, .... As a result, the strain free from the influence of the restraint state at each site in a heated state is calculated by $(\epsilon_1-\epsilon_2)$.

Stress $\sigma$ is expressed as:

$$\sigma=(\epsilon_1-\epsilon_2)E,$$

wherein E is a Young's modulus of the actual heat-resistant member (for instance, Young's modulus of spheroidal graphite cast iron at 800° C.).

Thus, the stress $\sigma$ can be calculated from the above formula: $(\epsilon_1-\epsilon_2)$. Designing and design modification of the manifold can be conducted based on the stress distribution thus obtained. Specifically, if a stress is concentrated in a particular spot or portion, it is necessary to strengthen that spot or portion, or to change the shape of its adjacent portion.

Since the stress distribution thus obtained is free from the influence of the restraint state, design modification of the manifold can be conducted with an extreme accuracy.

In some cases, since it is likely that a stress distribution obtained in a heated state and that obtained in a cooled state are not equal, it is desirable to measure a thermal strain distribution not only in a heated state but also in a cooled state for a more accurate measurement. For this purpose, the thermal strain distribution of the model is measured not only after heating the model from a low temperature to a high temperature but also after cooling the model from a high temperature to a low temperature. Specifically, the model is first heated in a free state and then placed in a restraint state by fixing its flange portions to table 11 by bolts 12. Next, the model 2 is cooled by blowing a cold air and then measured with respect to a strain $\epsilon'_1$ at each predetermined position at a low temperature in a restraint state. Further, after heating the model in a free state, it is cooled without restraint and measured with respect to a strain $\epsilon'_2$. $(\epsilon'_1-\epsilon'_2)$ is regarded as a strain free from the influence of the restraint state in a cooled state. Finally, the stress $\sigma'=(\epsilon'_1-\epsilon'_2)$ E is calculated.

The Young's modulus E is generally changeable with temperature and the thermal expansion coefficient of each material varies depending on the temperature. Accordingly, to estimate the stress distribution more accurately, temperature sensors 14 (shown schematically) are attached to the model 2 at positions near the strain gauges 4, 4, ..., and the strain and stress values are corrected by the temperature measured by the temperature sensors.

Specifically, the variation of Young's modulus with temperature inherently differs among various materials. Accordingly, the Young's modulus E' of an actual metal material is measured at each temperature corresponding to the measurement temperature of the model 2 in advance, and the Young's modulus E' is used to calculate the stress $\sigma=\epsilon E'$.

Figure 2:
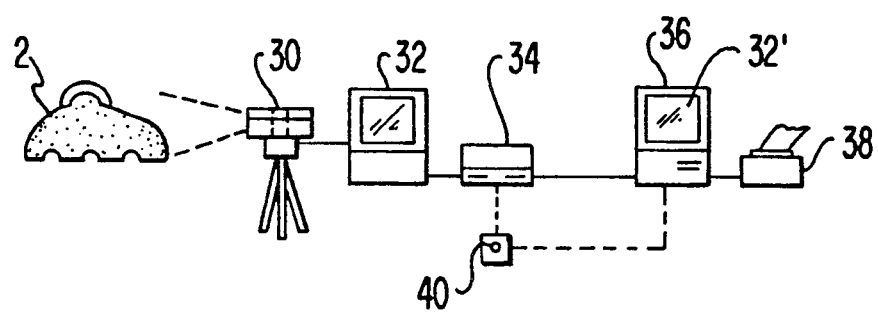
FIG. 2 is a schematic view showing a thermal image-analyzing apparatus for measuring a temperature distribution of the model.

The temperature distribution of the model 2 is detected desirably by a thermal image-analyzing apparatus simultaneously with measuring the strain distribution. The thermal image-analyzing apparatus comprises, as shown in FIG. 2, an infrared camera 30 for detecting the thermal distribution of the model 2, a display 32 for showing the thermal distribution as thermal image in color, a personal computer 36 connected to the display 32 via a frame recorder 34 and having a display 32' for showing the thermal image, and a color printer 38 for providing a printed output of the thermal image. The personal computer 36 conducts data analysis, too. By achieving an on-line connection between the frame recorder 34 and the personal computer 36, information on the thermal image can be obtained on real time. Alternatively, an off-line connection can also be used such that the thermal image information is stored in a floppy disk 40 in the frame recorder 34 and the information is read through a disk drive of the personal computer 36. By observing the temperature distribution in this manner, efficient modification of a model design can be conducted.

The present invention will be described in further detail by the following Examples.

EXAMPLE 1

As shown in FIG. 1, a model 2 of an exhaust manifold was produced from a polyurethane foam ("KM-60" manufactured by Kinuura Kogyo K. K.), and a plurality of (seven) resistance wire strain gauges 4, 4, ... were attached by an adhesive to a side surface of the model 2 at predetermined positions shown by "a" –"g." Using bolts 12 made of the same polyurethane foam as the model 2, flanges of the model 2 were fixed onto table 11 at positions of bolt apertures 10, 10, .... Next, a hot air was introduced by a drier into the model 2 through four ports 8, 8, ... from below.

The surface temperature of the model 2 reached about 50° C. after 10 seconds, and heating was stopped to measure a strain $\epsilon_1$ at each gauge position.

The bolts were then detached from the model 2, leaving the model 2 on the table without restraint, and it was similarly heated to measure a strain $\epsilon_2$ at each gauge position.

Next, the model 2 was heated to about 50° C. without restraint and fixed by bolts onto table 11. In this restraint state, a cold air was introduced into the model 2 by a drier to cool the model 2. When the surface temperature of the model 2 reached about 20° C., cooling was stopped to measure a strain $\epsilon'_1$ at each gauge position.

Similarly, after heating to about 50° C. without restraint, the model 2 was cooled in a free state (without restraint) to measure a strain $\epsilon'_2$.

Measurement Conditions:
$\epsilon_1$: restraint, heated
$\epsilon_2$: free, heated
$\epsilon'_1$: restraint, cooled
$\epsilon'_2$: free, cooled $(\epsilon_1 - \epsilon_2)$ and $(\epsilon'_1 - \epsilon'_2)$ at each gauge position are shown in table 1.

Young's modulus E used was 17000 kgf/mm$^2$, as a Young's modulus of spheroidal graphite cast iron at 800° C., and a stress $\sigma$ or $\sigma'$ at each predetermined position was calculated from the formulae:

$$\sigma = (\epsilon_1 - \epsilon_2)E, \text{ or}$$

$$\sigma' = (\epsilon'_1 - \epsilon'_2)E.$$

The results are shown in Table 1.

Incidentally, it is known that when strain gauges are adhered to a model, most of the expansion of the model is absorbed by the expansion of an adhesive used, and that a thermal expansion measured by the strain gauge is 1/14.8 of that of the model itself. Accordingly, the values of $(\epsilon_1 - \epsilon_2)$ and $(\epsilon'_1 - \epsilon'_2)$ are those obtained by multiplying the measured strain values by 14.8. In Table 1, a stress with a minus (−) symbol means "compression stress," and a stress with a plus symbol (+) means "tensile stress."

TABLE 1

| | When Heated | | | | When Cooled | | | |
|---|---|---|---|---|---|---|---|---|
| | Before Modification of Model Design | | After Modification of Model Design | | Before Modification of Model Design | | After Modification of Model Design | |
| Measurement Site | Strain $\epsilon_1-\epsilon_2$ ($\times 10^{-6}$) | Stress $\sigma$ | Strain $\epsilon_1-\epsilon_2$ ($\times 10^{-6}$) | Stress $\sigma$ | Strain $\epsilon'_1-\epsilon'_2$ ($\times 10^{-6}$) | Stress $\sigma'$ | Strain $\epsilon'_1-\epsilon'_2$ ($\times 10^{-6}$) | Stress $\sigma'$ |
| a | −888 | −15.1 | −474 | −8.6 | 222 | +3.8 | 1095 | +18.6 |
| b | −2176 | −37.0 | −562 | −9.6 | 1613 | +27.4 | 1391 | +23.6 |
| c | −1983 | −33.7 | −429 | −7.3 | 2412 | +41.0 | 858 | +14.6 |
| d | −2383 | −40.5 | −133 | −2.3 | 2264 | +38.5 | 829 | +14.1 |
| e | −1243 | −21.1 | 148 | +2.5 | 1894 | +32.2 | 607 | +10.3 |
| f | −1346 | −22.9 | −385 | −6.5 | 1110 | +18.9 | 725 | +12.3 |
| g | −1539 | −26.1 | −355 | −6.0 | 1110 | +18.9 | 636 | +10.8 |

Note: Unit of stress $\sigma$, $\sigma'$ is kgf/mm$^2$.

It is clear from Table 1 that there are relatively large strains at positions b, c, d and e, where there is a recess for providing a space for a tool for threading a flange bolt 10. Thus, the model 2 was somewhat elongated vertically without changing a cross-section area of each tubular portion extending from a flange 10, thereby reducing a space for a tool.

After this modification of the model design, the strain values $\epsilon_1$ measured when heated in a restraint state, the strain values $\epsilon_2$ measured when heated in a free state, the strain values $\epsilon'_1$ measured when cooled in a restraint state, and the strain values $\epsilon'_2$ measured when cooled in a free state were obtained in the same manner as above. The values of $(\epsilon_1 - \epsilon_2)$ and $(\epsilon'_1 - \epsilon'_2)$, and the calculated values of stresses $\sigma$, $\sigma'$ are also shown in Table 1.

As is clear from the comparison of each stress value, the overall stress was reduced by the modification of the model design.

At the same time of the above stress measurement, the temperature distribution of the model 2 was measured when heated and shown on a display as a thermal image by using an infrared camera ("TVS3000" manufactured by Nippon Avionics K.K.). The thermal image was also provided as a printer output in color.

As a result, it was found that heat spots were decreased after the modification of a model design, resulting in a more uniform thermal distribution. Particularly, it was confirmed that heat spots in the recess for a tool were removed.

As described above, since the thermal stress estimating method of the present invention uses a model formed by a heat-insulating, high-thermal expansion material to generate a low temperature distribution on its surface, strain gauges for detecting a thermal strain may be those commercially available. Accordingly, linearity of strain data can be ensured in a wide temperature range, with good reliability even in portions having small radii of curvature. As a result, the thermal stress distribution measurement is relatively easy on members having such shapes that thermal stress distribution measurements would be difficult if their polyurethane models are not used.

In addition, since a strain is measured on the model both in a restraint state and in a free state and their difference is evaluated, the influence of the restraint condition can be excluded. Therefore, the modification of a model design per se can be evaluated easily, and the thermal stress distribution of the heat-resistant member can be obtained with high reliability.

What is claimed is:

1. A method of manufacturing a heat resistant member, part or the whole of which is to be heated to a high temperature, comprising the steps of:
    designing the shape of the heat-resistant member, the step of designing including the substep of estimating thermal stress of the heat-resistant member by steps comprised of (i) heating to heated states a model formed by a high-thermal expansion material and having a shape similar to a desired shape of said heat-resistant member while said model is in a restraint state and also in a free state, respectively, said high-thermal expansion material being different from the material of the member being modeled and having a thermal expansion coefficient greater than that of the material of the member being modeled; (ii) measuring the strain of said model at each of a plurality of predetermined positions in the heated states by strain gauges adhered to the predetermined position of said model; and (iii) calculating a stress at each predetermined position from the difference in measured strain values between said restraint state and said free state, thereby estimating the stress of said heat-resistant member in a heated state; and
    casting said heat-resistant member to the designed shape.

2. A method according to claim 1, wherein the temperature of said model is measured by a temperature sensor at each of the predetermined positions, and the strain values of said model measured by strain gauges are corrected by the temperature at each respective predetermined position, thereby calculating the true stress values of said model at a predetermined temperature.

3. The method according to claim 1, wherein said high-thermal expansion material is a foam material.

4. The method according to claim 3, wherein said foam material is a polyurethane foam.

5. The method according to claim 1, wherein during measurement of the strain, the temperature distribution of the model is determined by thermal imaging.

6. A method of manufacturing a heat-resistant member, part or the whole of which is to be heated to a high temperature, comprising the steps of:
    designing the shape of the heat-resistant member, the step of designing including the substep of estimating thermal stress of the heat-resistant member by steps comprised of (i) cooling to cooled states a model formed by a high-thermal expansion material and having a shape similar to a desired shape of said heat-resistant member while said model is in a restraint state and also in a free state, respectively, from a high temperature to a low temperature, said high-thermal expansion material being different from the material of the member being modeled and having a thermal expansion coefficient greater than that of the material of the member being modeled, (ii) measuring the strain of said model at each of a plurality of predetermined positions in said cooled states by strain gauges adhered to the predetermined positions of said model, and (iii) calculating a stress at each predetermined position from the difference in measured strain values between said restraint state and said free state, thereby estimating the stress of said heat-resistant member in a cooled state; and
    casting said heat-resistant member to the designed shape.

7. The method according to claim 6, wherein the temperature of said model is measured by a temperature sensor at each of the predetermined positions, and the strain values of said model measured by said strain gauges are corrected by the temperature at each respective predetermined position, thereby calculating the true stress value of said model at a predetermined temperature.

8. The method according to claim 6, wherein said high-thermal expansion material is a foam material.

9. The method according to claim 8, wherein said foam material is a polyurethane foam.

10. The method according to claim 6, wherein during measurement of the strain, the temperature distribution of the model is determined by thermal imaging.

11. A method of manufacturing a heat-resistant member, part or the whole of which is to be heated to a high temperature, comprising the steps of:
    designing the shape of the heat-resistant member, the step of designing including the substep of estimating the thermal stress of the heat-resistant member by steps comprised of (i) heating to heated states a model formed by a high-thermal expansion material and having a shape similar to a desired shape of said heat-resistant member while said model is in a restraint state and also in a free state, respectively, from a low temperature to a high temperature, said high-thermal expansion material being different from the material of the member being modeled and having a thermal expansion coefficient greater than that of the material of the member being modeled, (ii) measuring the strain of said model at each of a plurality of predetermined positions in said heated states, (iii) cooling to cooled states said model with and without restraint, (iv) measuring the strain of said model at each of the predetermined positions in said cooled states, and (v) calculating the stress at each predetermined position in said heated states and in said cooled states, from the differences in measured strain values between said restraint state and said free state, thereby estimating the stresses of said heat-resistant member both in a heated state and in a cooled state; and
    casting said heat-resistant member to the designed shape.

12. The method according to claim 11, wherein the temperature of said model is measured by a temperature sensor at each of the predetermined positions, and the strain values of said model measured by said strain gauges are corrected by the temperature at each respective predetermined position, thereby calculating the true stress value of said model at a predetermined temperature.

13. A method according to claim 11, wherein said high-thermal expansion material is a foam material.

14. The method according to claim 13, wherein said foam material is a polyurethane foam.

15. The method according to claim 11, wherein during measurement of the strain, the temperature distribution of the model is determined by thermal imaging.

* * * * *